United States Patent [19]
O'Neil et al.

[11] Patent Number: 5,683,472
[45] Date of Patent: Nov. 4, 1997

[54] FEMORAL STEM ATTACHMENT FOR A MODULAR KNEE PROSTHESIS

[75] Inventors: Michael J. O'Neil, West Barnstable; John E. Slamin, Wrentham, both of Mass.

[73] Assignee: Johnson & Johnson Professional, Inc., Raynham, Mass.

[21] Appl. No.: 581,043

[22] Filed: Dec. 29, 1995

[51] Int. Cl.$^6$ .................................................. A61F 2/38
[52] U.S. Cl. ........................... 623/20; 623/18; 623/16; 623/23; 623/22; 606/65; 606/73
[58] Field of Search ........................... 623/16, 18, 20–23; 606/65, 73

[56] References Cited

U.S. PATENT DOCUMENTS

| | | | |
|---|---|---|---|
| 4,822,366 | 4/1989 | Bolesky | 623/20 |
| 4,904,110 | 2/1990 | Klein | 403/379 |
| 4,985,037 | 1/1991 | Petersen | 623/20 |
| 5,002,581 | 3/1991 | Paxson et al. | 623/18 |
| 5,127,914 | 7/1992 | Calderale et al. | 606/65 |
| 5,133,760 | 7/1992 | Petersen et al. | 623/20 |
| 5,152,796 | 10/1992 | Slamin | 623/20 |
| 5,290,313 | 3/1994 | Heldreth | 623/20 |
| 5,326,359 | 7/1994 | Oudard | 623/20 |
| 5,336,225 | 8/1994 | Zang | 606/73 |
| 5,507,824 | 4/1996 | Lennox | 623/22 |
| 5,556,433 | 9/1996 | Gabriel et al. | 623/20 |

FOREIGN PATENT DOCUMENTS

| | | | |
|---|---|---|---|
| 0529408 | 3/1993 | European Pat. Off. | A61F 2/38 |
| 473375 | 3/1929 | Germany . | |

OTHER PUBLICATIONS

Johnson & Johnson Orthopaedics Research & Development "P.F.C.® Modular Knee System Research Data and Laboratory Testing", cover and pp. 8, 36 & 37 (1989).

Primary Examiner—John G. Weiss
Assistant Examiner—Francis K. Cuddihy
Attorney, Agent, or Firm—Nutter, McClennen & Fish, LLP

[57] ABSTRACT

A modular knee prosthesis includes a femoral component having a pair of laterally spaced apart condylar portions each having a superior, articulation surface and an inferior surface. A boss structure is disposed between and connects the condylar portions. The boss structure has an inferior surface that extends generally horizontally in the transverse plane, and an opposed superior surface. The boss structure has an aperture having a selected configuration formed therein and which extends between the inferior and superior surfaces. The boss structure has formed on the superior surface thereof a positioning structure, e.g., a plurality of grooves, that define one or more positions, in the transverse plane, in which to seat a femoral stem assembly. A washer is mountable upon the superior surface of the boss structure and over a portion of the boss aperture. The washer includes at least one detent that cooperates with the positioning structure to secure the washer in one of the mounting positions.

24 Claims, 3 Drawing Sheets

FEMORAL STEM ATTACHMENT FOR A MODULAR KNEE PROSTHESIS

BACKGROUND OF THE INVENTION

This invention relates to implantable joint prostheses, and more particularly to femoral stem assemblies for use with modular knee joint prostheses employed during knee arthroplasty procedures.

Knee arthroplasty is a well known surgical procedure by which a diseased and/or damaged natural knee joint is replaced by a prosthetic knee joint. Typical knee prostheses include a tibial component, a femoral component, a femoral stem assembly and a patellar component. The femoral component generally includes a pair of spaced apart condylar portions, the superior surfaces of which articulate with a portion of the tibial component. The femoral stem assembly provides lateral stability to the replaced knee joint, and typically includes a member that mounts within the medullary canal of a distal portion of a femur. The stem is typically coupled to the femoral component by a specialized collar and bolt.

Knee joint prostheses are available as modular assemblies to reduce the number of individual components that must be purchased and stocked, and to reduce the associated component handling time by a surgeon during the arthroplasty procedure. An example of a prior art modular knee prosthesis is described in U.S. Pat. No. 5,152,796 (Slamin). The Slamin patent describes a modular knee prosthesis that includes a femoral component and a series of bolts that attach to and extend from the femoral component at various angles corresponding to different valgus angles. The valgus angle is defined as the angle between the center line of the femur and the vertical axis connecting the distal femur and the center of the femoral head. Typical valves of the valgus angle are between 5° and 9°. The prosthesis also includes a plurality of femoral stems having different lengths and diameters.

Despite existing modular knee joint prostheses, there remains a need for a modular knee joint prosthesis that has sufficient versatility to accommodate differing patient anatomy and joint conditions. Many modern modular knee prostheses are characterized by a large number of components with little or no part interchangeability. Such systems tend to increase purchasing costs because of part waste. Additionally, the numerous parts must be handled and stocked, thus increasing costs associated with inventory control and management.

Another drawback of some existing modular knee prostheses is that they provide insufficient versatility to accommodate differing patient anatomies. Patients typically have different femoral anatomies and thus require stems of different sizes and curvatures. Additionally, the mounting location or origination point of the stem relative to the femoral component varies among patients. Many known modular knee systems attempt to overcome these drawbacks by utilizing specialized parts and related mounting hardware. These specialized parts, however, add to the overall piece count and cost of the system. Such items risk complicating the surgical procedure due to the time required to assemble the artificial knee joint.

It is thus an object of the invention to provide a modular knee prosthesis having sufficient versatility to accommodate various patient anatomies and joint conditions while maintaining a relatively low component piece count. It is another object of the invention to provide a modular knee prosthesis having components that are physiologically and geometrically compatible with different patient anatomical geometries and conditions. Still another object of the invention is to provide a modular knee prosthesis that can accommodate different femoral stems. Yet another object of the invention is to provide a modular knee prosthesis that can vary the origination point of the femoral stem relative to the femoral component during the surgical procedure. A further object of the invention is to provide a modular knee prosthesis that is relatively easy to use. Other general and more specific objects of the invention will in part be apparent from the drawings and description which follow.

SUMMARY OF THE INVENTION

The present invention relates to a modular knee joint prosthesis having improved versatility while reducing the overall component piece count. Components of the modular prosthesis of the invention are able to be used with both right and left side prostheses.

The modular knee prosthesis of the invention includes a femoral component having a pair of laterally spaced apart condylar portions each having a inferior, articulation surface and an superior surface. A boss structure is disposed between and connects the condylar portions. The boss structure has an superior surface that is generally horizontally oriented in the transverse plane, and an opposed inferior surface. An aperture, formed in the boss structure, extends between the inferior and superior surfaces thereof. The prosthesis further includes a bolt having head and shaft portions, an elongate stem member, and appropriate positioning structure.

The positioning structure locates the femoral stem at one or more mounting positions in the transverse plane. The mounting positions are defined as those positions formed along the boss aperture in the transverse plane, and spaced apart from each other in the anterior-posterior direction, where the stem assembly is secured, by an appropriate securing structure, to the femoral component. Thus, the aperture, which preferably is elongated, provides a potentially infinite number of discrete origination points in the transverse plane. The term "origination point" is intended to mean the point on the superior surface of the boss structure from which the bolt shaft protrudes when mounted in the aperture of the femoral component.

According to one aspect, the positioning structure comprises one or more surface features that are formed on the boss structure and a mating element that is directly or indirectly matable with the femoral stem. The mating element has at least one surface feature that is engageable and interlockable with the surface feature of the boss. According to one embodiment, the boss surface feature comprises one or more grooves and the mating element, e.g., a washer, has a detent that is adapted to seat in one of the grooves. The grooves preferably extend in the medial-lateral direction and are spaced apart from one another in the anterior-posterior direction.

According to another aspect of the invention, the boss structure includes position indicia formed on the superior surface of the boss structure. The positioning indicia provide a visual indication of at least some of the mounting positions of the femoral stem.

According to another aspect, the modular knee prosthesis includes a collar having a proximal end for mounting to the distal end of the femoral stem member and a distal end for mounting on the superior surface of the boss structure. The collar has position markings that cooperate with the positioning indicia of the boss structure to visually indicate the femoral stem mounting position.

According to still another aspect, the collar and stem include orientation indicia, which cooperate to visually indicate the position in the sagittal plane of a curved femoral stem member. The knee prosthesis of the invention accommodates differing patient anatomies by allowing a curved femoral stem to be affixed in a selected position relative to the patient's femur. Thus, a surgeon can tailor the modular prosthesis to be compatible with a patient's unique anatomy by first selecting the desired orientation of the stem member via the orientation indicia, and then positioning the stem assembly in the transverse plane at the appropriate mounting position by way of the positioning indicia.

Although illustrated as a modular unit, those of ordinary skill will recognize that the individual components of the assembly can be provided separately.

BRIEF DESCRIPTION OF THE DRAWINGS

The foregoing and other objects, features and advantages of the invention will be apparent from the following description and the accompanying drawings, in which like reference characters refer to the same parts throughout the different views.

DETAILED DESCRIPTION OF THE INVENTION

Figure 1:
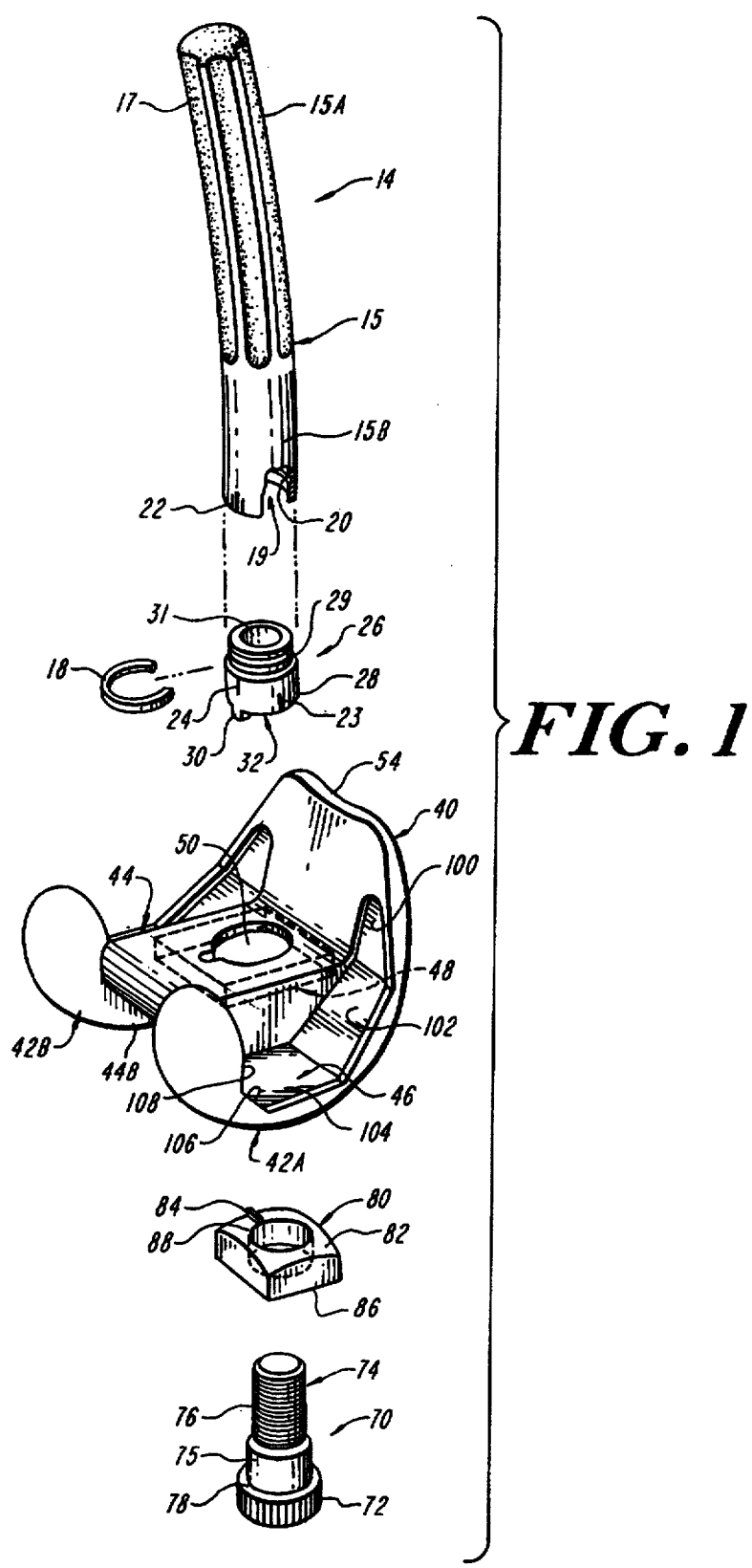
FIG. 1 is an exploded perspective view of a modular knee prosthesis according to the present invention.

As illustrated in FIG. 1, the modular knee prosthesis 10 of the invention includes a femoral stem 14, a collar 26, a femoral component 40, a washer 80, and a securing bolt 70. Components of the illustrated modular knee prosthesis 10 are suitable for use in both right and left side prostheses.

Figure 2:
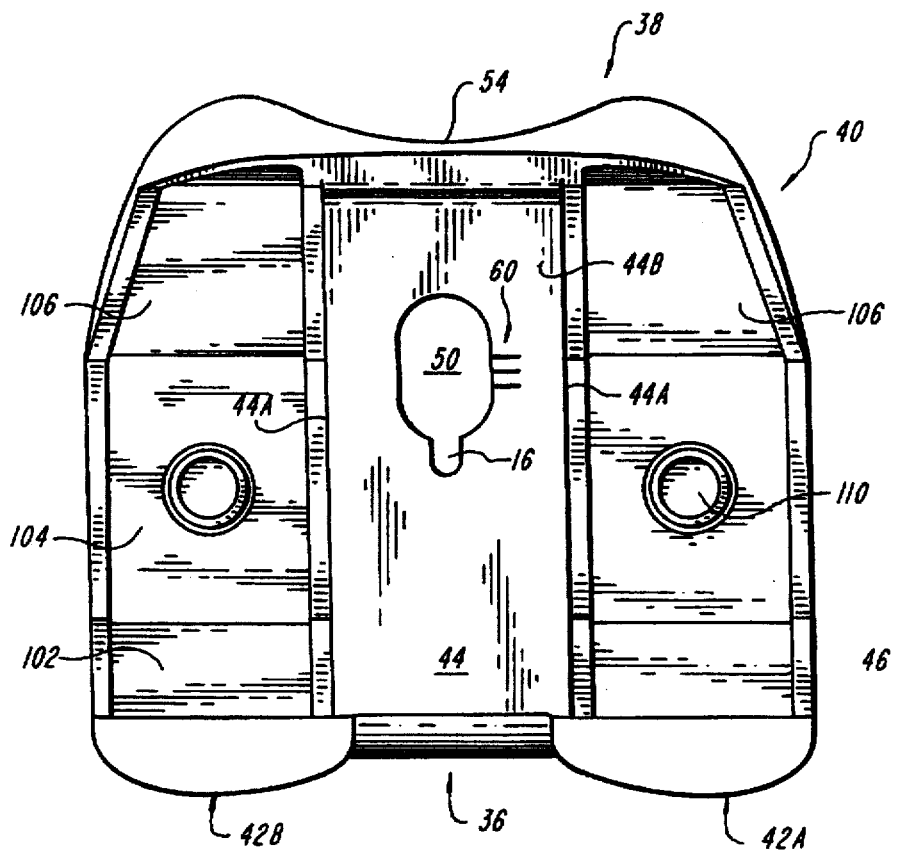
FIG. 2 is a plan view of the superior surface of the femoral component of FIG. 1.
Figure 3:
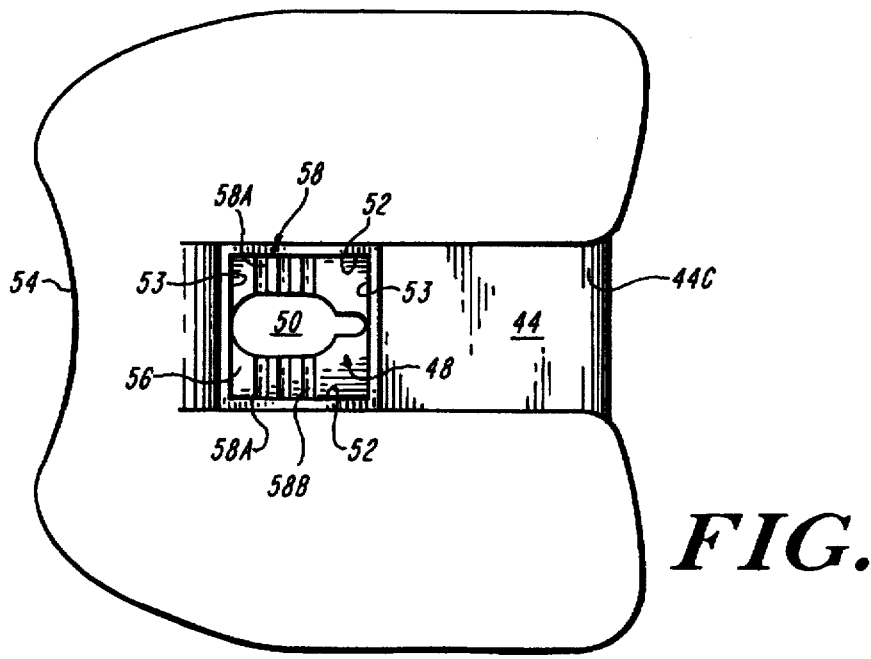
FIG. 3 is a plan view of the inferior articulation surface of the femoral component of FIG. 1.

Referring to FIGS. 1 through 3, the femoral component 40 has a pair of spaced condylar portions 42A, 42B that are connected by an intercondylar boss structure 44. The femoral component 40 has a inferior articulation surface 45 and an opposed superior surface 46. Further, the femoral component 40 has a posterior side 36 and an anterior side 38. The anterior side 38 of the femoral component 40 includes a patellar groove 54, which seats a patellar prosthetic component (not shown). The inferior surfaces 45 of the curved condylar portions 42A, 42B articulate with a prosthetic tibial component (not shown) mounted on the head of the tibia, in a manner well known in the art.

The boss structure 44 has a pair of substantially vertical side walls 44A that are generally orthogonal to a top, superior surface 44B and a bottom inferior surface 44C. The top surface 44B is substantially horizontally oriented and extends in the transverse plane. The boss 44 further has a cavity 48 that is formed within the bottom inferior surface 44C. The cavity 48 has a substantially rectangular shape and has a pair of medial-lateral side walls 52 and a pair of anterior-posterior side walls 53. The cavity further includes a substantially flat endwall 56 that seats the top surface 82 of the washer 80.

An elongated aperture 50, preferably elongated in the anterior-posterior direction, is formed in the endwall 56 of cavity 48 and extends between the inferior superior surfaces 45, 46 of the boss structure 44. As illustrated in FIG. 3, and as shown in phantom in FIG. 1, the cavity extends in the direction of the aperture to allow a bolt to move easily within the aperture. The shape of the aperture can be elliptical, oval, spherical, or of any other suitable shape that allows a sufficient amount of translation of the bolt shaft 74 of the bolt when the bolt is mounted within the aperture 50.

The transverse plane is defined as the horizontal plane that extends through the knee of an upright subject and that is orthogonal to both the coronal plane and the sagittal plane, as will be appreciated by those having ordinary skill in the art.

The elongated shape of the cavity 48 and of the aperture 50 provide sufficient space for the bolt shaft 74 to translate therealong in the anterior-posterior direction. This freedom of movement of the bolt 70 within the aperture 50 in the transverse plane provides a virtually infinite number of mounting positions for the stem assembly, e.g., the stem member 14 and the collar 26.

The endwall 56 of the cavity 48 has formed thereon a series of surface features 58, e.g., grooves or protrusions, that preferably extend in the medial-lateral direction and are spaced in the anterior-posterior direction. The surface feature 58 of the boss structure 44 cooperates with another, complementary surface feature 84 formed on the top surface 82 of the mating element, e.g., the washer 80, to position the stem 14 at one of the mounting positions, as described further below. The surface feature 58 of the boss 44 can be in the form of an indentation or a raised structure that is located on either the superior or inferior surface 46, 45 of the boss 44. It is understood that surface features 58, 84 are intended to be complementary. Thus, if surface features 58 are in the form of grooves, surface feature 84 will be in the form of a protrusion dimensioned to fit within the grooves. Although the end wall of the femoral component of the drawings includes three grooves, those of ordinary skill in the art will recognize that any number of grooves can be formed in the boss superior surface.

Figure 4:
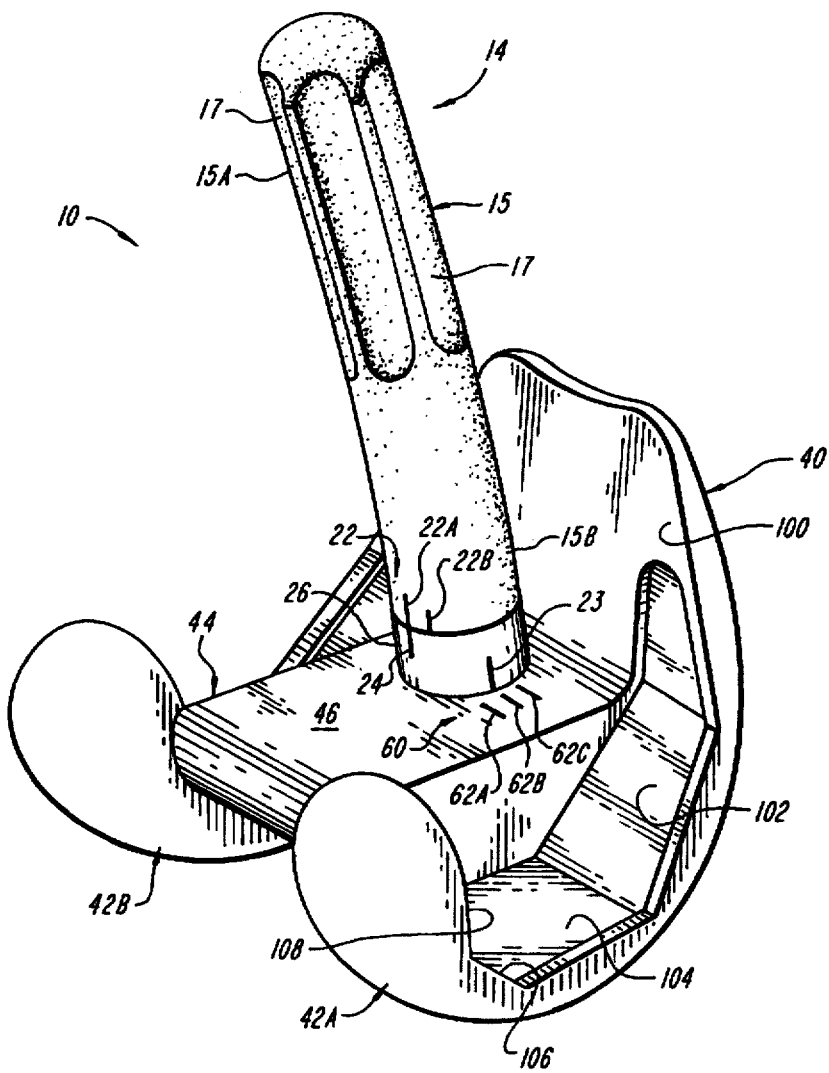
FIG. 4 is an assembled view of the modular knee prosthesis of FIG. 1.

With reference to FIGS. 1 through 4, and particularly to FIG. 4, the superior surface 46 of the boss 44 has position indicia 60 at locations relative to the surface feature 58 formed on the boss inferior surface 45. The position markings 60 visually indicate one or more mounting positions in the transverse plane. According to one practice, the collar 26 includes a position marking 23 that cooperates with the boss position indicia 60 to visually indicate the mounting position of the stem assembly in the transverse plane.

The illustrated boss indicia 60 preferably include a linear succession of lines 62A–62C that represent different spatial stem mounting locations. For example, line 62B can be used to indicate that a stem is mounted without offset. Line 62A can be used to indicate a stem mounting which is offset by 2 mm in the posterior direction. Likewise, line 62C can be used to indicate a stem mounting which is offset by 2 mm in the anterior direction. Thus, the position indicia 60 visually indicate the mounting position of the femoral stem. One having ordinary skill will readily appreciate that any number of position indicia can be formed on the superior surface 46, and that each indicia marking corresponds to a different femoral stem mounting position.

The superior surface 46 of the condylar portions 42A, 42B includes a series of connected integral surfaces that extend between the anterior and posterior sides of the femoral component 40. Referring to FIGS. 1, 2 and 4, the superior surface 46 of each condylar portion 42A and 42B comprises an anterior flange 100, an anterior chamfer 102, a substantially horizontal surface 104, a posterior chamfer 106, and a posterior flange 108. The horizontal surface 104 of each condylar portion 42A, 42B has an indentation 110 that extends partly into the superior surface 46 of each condylar portion. The indentation 110 allows the surgeon to grasp and handle the femoral component 40 via a suitable handling instrument.

Figure 6:
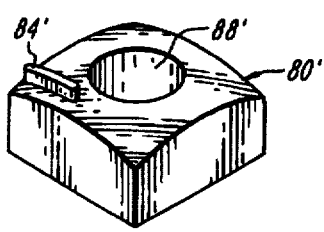
FIG. 6 is a perspective view of an alternate embodiment of a washer useful with the invention.

FIGS. 1 and 6 illustrate the washer 80 useful with the present invention. The washer 80 includes a top portion 82 and an opposed bottom portion 86. A non-threaded central aperture 88 extends between the top and bottom surfaces. A surface feature 84, e.g., a detent, is formed on at least one of the washer surfaces, e.g., the top surface 82. The surface feature 84 is preferably located at a substantially centrally located position on the washer top surface 82, and cooperates with the surface feature 58 of the boss to position the femoral stem 14 at a selected mounting position within the transverse plane, and to prevent the femoral stem assembly from slipping from the desired mounting position.

In the embodiment of FIG. 1, the central location of the raised surface feature 84 allows the washer 80 to seat easily in one of the surface features 58 formed along the endwall 56 of the boss. For example, as illustrated in FIG. 3, if it is desirable to locate the washer 80 in the posterior direction, the detent 84 can be mounted within the posterior-most groove, e.g., groove 58B. Similarly, if it is desirable to mount the washer in the anterior-most direction, the detent 84 can be mounted within the anterior-most groove, e.g., groove 58A. The washer can be any conventional biocompatible mechanical washer, and can be composed of a cobalt/chromium or titanium alloy, stainless steel, ultra-high molecular weight polyethylene, or high density polyethylene.

In an alternative embodiment, the raised surface feature 84' can be formed at a non-centrally located position, as illustrated in FIG. 6. As illustrated surface feature 84' is formed at an offset position measured relative to the central aperture 88' of the washer 80'. Similar to the washer 80 of FIG. 1, the offset surface feature 84' of the washer 80' allows the washer to seat at one of a plurality of mounting positions defined by the indented surface feature 58 formed in the endwall 56 of the boss 44. The offset surface feature 84' provides for plural mounting positions in the anterior-posterior direction by simply rotating the washer 80' to align the surface feature 84' with the indented surface feature 58 located at the desired position. The surface features 84 and 84' can thus be formed at selected locations on the washer that optimize placement of the femoral stem in the transverse plane at a series of desired stem mounting locations.

The offset surface feature 84' is particularly useful in modular knee prostheses that provide only a single indented surface feature 58 on the endwall 56 of the boss structure 44. The offset surface feature 84' cooperates with the single indented feature to form multiple mounting positions. In one embodiment of the invention, the washer 80' contains an offset surface feature 84' on a first surface and a non-offset surface feature 84 on the opposing surface. This construction enables a single washer to position the femoral stem at least at three locations in the transverse plane, e.g., at 0 mm offset and at the 2 mm anterior and posterior offset positions. When multiple indented surface features are formed on the endwall 56, the femoral stem 14 can be positioned at three or more positions in the transverse plane.

According to another embodiment of the invention, the washer 80 contains an indented surface feature such as a groove rather than a raised surface feature such as a detent. Such a groove can be positioned at either or both the offset and non-offset locations. In this embodiment, the endwall 56 of the boss structure 44 has formed thereon a linear series of raised surface features sized to seat within the washer groove. Those of ordinary skill in the art will readily recognize that other suitable permutations to the illustrated washer design exist.

The elongated aperture 50, grooves 58 and washer detent 84 cooperate to optimize the stem location within the intramedullary canal of the femur by allowing the surgeon to select the proper mounting position for the stem assembly. The ability to optimize the stem location ensures that the proper mechanical stresses are transferred along the femur, without overloading a particular portion of bone. Additionally, the proper alignment of the stem assembly with the femoral component ensures that the condyles properly contact and articulate with the tibial bearing member.

With reference to FIG. 1, the illustrated securing bolt 70 preferably includes a head portion 72 having a washer-engaging surface 78 and a shaft portion 74 that extends outwardly therefrom. The shaft portion 74 preferably has an unthreaded shaft portion 75 disposed adjacent to the head portion 72, and an upper, threaded portion 76 disposed adjacent to the unthreaded portion 75. The unthreaded shaft portion 75 preferably has an outer diameter that is less than the outer diameter of the head portion 72. The upper, threaded portion 76 preferably has a diameter equal to or less than the diameter of the unthreaded portion 75.

The collar 26 has a main body that includes a distal portion 28 and an adjacent proximal portion 29 which has a threaded outer surface. The proximal portion 29 is preferably sized to mate with femoral stems 14 having various diameters, including diameters of between about 10 mm and about 24 mm. The distal portion 28 of the collar has an anti-rotation protrusion 30 that extends downwardly from a boss-engaging surface 32. The anti-rotation protrusion 30 preferably seats in an appropriate cut-out section 16 that is formed within the boss aperture 50, as shown in FIG. 2. For example, when the boss-engaging surface 32 of the collar 26 is placed in contact with the boss superior surface 46, the anti-rotation protrusion 30 seats within the aperture to prevent unwanted rotation of the collar 26 when the femoral stem 14 is tightened on the bolt shaft 74. This feature is desirable since it enables the collar to be locked in a selected position and location during assembly of the knee joint components. Those of ordinary skill will appreciate that the protrusion 30 can also be formed as an indented surface feature.

Figure 5:
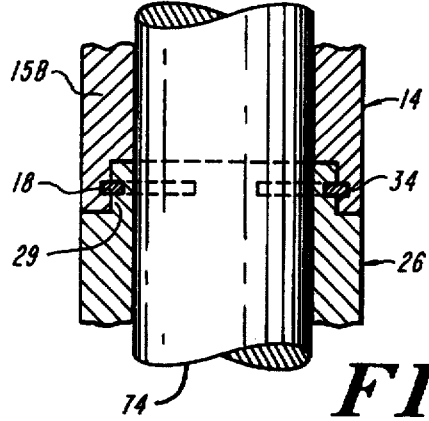
FIG. 5 is a detailed view, partly in cross-section, of the stem member and collar components of the knee prosthesis of FIG. 1.

The collar 26 further includes a circumferential slot 34 that, in conjunction with a slot 20 formed along the inner portion of the stem 14, seats a lock ring 18 in the manner illustrated in FIG. 5. The lock ring secures the stem 14 to the collar 26 when the two components are assembled together. A central aperture 31 within collar 26 is sized to seat the bolt shaft 74 and allows the bolt shaft to pass therethrough.

With reference to FIGS. 1 and 4, the collar 26 further includes position marking 23 formed on the outer surface of the collar distal portion 28. The position marking 23 in conjunction with the position indicia 60 of the boss 44 visually indicate the mounting position, in the transverse plane, of the femoral stem assembly. Specifically, aligning the position marking 23 with one of the position indicia 60 formed on the superior surface 46 of the boss structure 44, as shown in FIG. 4, indicates whether the stem assembly is positioned in the anterior direction, the posterior direction, or at an intermediate position, in the transverse plane.

By way of example, aligning the position marking 23 of the collar with position marking 62A positions the femoral stem assembly in the posterior direction in the transverse plane. Similarly, aligning the position marking 23 with the marking 62C positions the stem assembly in the anterior direction. The position marking 62B preferably represents an intermediate, no-offset position.

A significant advantage of providing the position markings on the collar 26 and the boss structure 40 is that they allow the surgeon, at a glance, to choose a desired mounting position for the stem 14, while concomitantly providing a flexible knee prosthesis for which immediate stem adjustments can be made in the course of surgical procedures.

The collar 26 further includes orientation indicia 24 formed on the outer distal portion 28 of the collar 26 at a location circumferentially spaced from the position marking 23. The orientation indicia 24 cooperate with orientation markings 22 formed on the stem 14 to indicate the relative position of the femoral stem 14 in the sagittal plane. This feature of the invention is discussed in further detail below.

Referring again to FIGS. 1 and 4, the femoral stem 14 has an elongate body 15 that extends along a longitudinal axis. A series of circumferentially spaced flutes 17 are formed along a proximal portion 15A of the body 15. The flutes 17 inhibit rotation of the stem within the medullary canal of the femur. The distal portion 15B of the stem body 15 further has a collar and bolt-receiving aperture 19 that seats the proximal portion 29 of the collar 26 and the portion of the bolt shaft 74 that extends beyond the proximal surface 29 of the collar 26 (see FIG. 5). The aperture 19 preferably has a threaded portion, on an interior wall thereof, that mates with a threaded portion 76 of the bolt shaft 74.

The stem 14 is preferably curved along the length of the stem main body 15 to simulate the natural bow of the human femur. The stem can be formed with a variety of curvatures to accommodate differing patient anatomies. The femoral stem is also suitable for use, without modification, in both left and right side prostheses.

As noted above, the femoral stem 14 also includes orientation markings 22 which help indicate the relative position of the curved stem member in the sagittal plane. Markings 22 preferably include a plurality of vertical lines that represent separate discrete spatial positions. As illustrated in FIG. 4, a longer central line 22A is disposed between a pair of shorter vertical lines 22B. The longer central line preferably indicates the position of the stem relative to the collar 26. The stem orientation markings 22 are preferably used in conjunction with the collar orientation indicia 24 to positively and easily position the femoral stem 14 in a selected position in the sagittal plane. For example, the central line 22A can be aligned with one of the orientation indicia 24 of the collar to orient the stem at a selected location. Thus, the stem position in the sagittal plane can be easily changed by aligning the orientation marking 22 with different ones of the orientation indicia 24. This feature allows the surgeon to utilize curved, as well as straight, femoral stem members.

The knee prosthesis of the invention is assembled as follows. First, the washer 80 is disposed within the elongated cavity 48 formed in the inferior surface 45 of the boss structure 44. The surface feature 84, formed on the top surface 82 of the washer 80, is then aligned with one of the surface features 58 formed in the cavity endwall. The surface features 58 are adjacent an elongated aperture 50 that extends between the inferior and superior surfaces of the boss.

According to a preferred practice, the femoral stem 14 and the collar 26 are secured together by the lock ring 18 at the manufacturing site. This pre-assembly of selected components is desirable since it reduces the number of parts that the surgeon has to assemble during the surgical procedure.

The collar 26 is then mounted on the superior surface 46 of the boss structure 44 at a desired location in the transverse plane, corresponding to the location of the washer 80, by aligning the position markings 23 formed on the collar 23 with one of the appropriate positioning indicia 60 formed on the boss. The positioning indicia 60 and position markings 23 cooperate to indicate the desired mounting position of the stem assembly. The mounting position can be adjusted by simply placing the surface feature 84 of the washer in a different indented surface feature, and by visually aligning the position marking 23 of the collar with the corresponding position indicia 60.

The anti-rotation protrusion 30 of the collar 26 preferably seats within the cut-out section 16 formed within the boss aperture 50 to prevent unwanted rotation of the collar during assembly. The cut-out section 16 preferably is oriented such that it is elongated in the anterior-posterior direction and opens onto the central boss aperture 50 to allow the collar 26 to mount at one of the plurality of mounting locations.

The distal portion 15B of the femoral stem 14 is then placed over the proximal portion of the collar 26. In this assembly, the proximal portion of the collar seats within the receiving end, e.g., distal end, of the stem, but is not rigidly captured therein. Thus, the stem, at least initially, is rotatable about the stem axis independent of the collar. This allows the stem to be properly positioned at a desired orientation in the sagittal plane, indicated by the orientation indicia formed on the collar 24 and the stem 22. Independent rotation of the stem enables the stem and/or collar to remain properly positioned.

When the desired stem mounting position in the transverse plane and the desired orientation in the sagittal plane are selected, the bolt 70 is then inserted from the inferior side of the femoral component 40 through the washer aperture 88, the boss aperture 50, and into the collar central aperture 31. The portion of the bolt shaft 74 that extends beyond the proximal end 29 of the collar is captured within the receiving aperture 19 formed in the distal portion 15B of the stem 14. When the bolt 70 is tightened, the stem 14 and the bolt head 72 are drawn together until the collar 26 is secured between the stem 14 and the boss structure 44.

The modular knee prosthesis of the invention thus provides an easy and effective technique for the surgeon to quickly and readily tailor the modular knee prosthesis to the patient. The prosthesis of the invention further provides a prosthesis that provides multiple positioning of the stem assembly in the transverse plane and multiple positioning of the curved stem in the sagittal plane, while reducing the overall piece count of the system.

It will thus be seen that the invention efficiently attains the objects set forth above, among those made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements concerning of the scope of the invention which, as a matter of language, might be said to fall therebetween. All cited references are incorporated herein by reference.

What is claimed is:

1. A modular knee prosthesis comprising:
   a femoral component having a pair of spaced apart condylar portions, each of the condylar portions having an inferior articulation surface and a superior surface, a generally horizontally oriented boss structure having an inferior surface and an opposed superior surface, and a boss aperture extending between the inferior surface and superior surface;
   a femoral stem component for mounting within the medullary canal of a distal portion of a patient's femur, the femoral stem component having a proximal end, and a distal end that is mountable to the boss structure;
   means for securing the femoral stem component in any one of a plurality of desired transverse plane mounting positions; and
   an elongate bolt having a head portion and a neck portion, the neck portion being adapted to mount within the boss aperture and to extend into a distal portion of the femoral stem component.

2. The knee prosthesis of claim 1 wherein the means for securing comprises
   one or more surface features associated with the boss structure; and
   a mating element directly or indirectly mountable to the femoral stem component, the mating element having at least one surface feature that is engageable and interlockable with one of the surface features associated with the boss structure.

3. The knee prosthesis of claim 2 further comprising a collar having a body portion and an aperture extending therethrough, the collar having a distal portion that mounts upon the superior surface of the boss structure and a proximal portion that is adapted to seat within the distal end of the femoral stem component.

4. The knee prosthesis of claim 2 wherein the surface features associated with the boss structure are disposed on the inferior surface of the boss structure.

5. The knee prosthesis of claim 4 wherein the surface features associated with the boss structure comprise a plurality of substantially parallel grooves that extend in a medial-lateral direction and which are spaced apart from one another in an anterior-posterior direction.

6. The knee prosthesis of claim 3 further including a plurality of anterior-posterior positioning indicia indicating the relative placement of the femoral stem component in a transverse plane.

7. The knee prosthesis of claim 6 wherein the plurality of anterior-posterior positioning indicia comprise
   relative position markings disposed on the superior surface of the boss structure, the relative position markings extending in a medial-lateral direction and being spaced apart from one another in an anterior-posterior direction; and
   at least one position indicator disposed on the collar such that the location of the position indicator on the collar and the relative position markings on the superior surface of the boss structure indicates a mounting position of the femoral stem component in the transverse plane.

8. The knee prosthesis of claim 1 wherein the femoral stem component is curved.

9. The knee prosthesis of claim 6 further comprising orientation indicia means for indicating the relative orientation of the femoral stem component in a sagittal plane.

10. The knee prosthesis of claim 9 wherein the orientation indicia means comprise
    a series of parallel first markings formed on the collar; and
    at least one second marking formed on the distal end of the femoral stem component;
    wherein the series of first markings and said at least one second marking have a relative position indicating the orientation of the stem component in a sagittal plane.

11. A modular knee prosthesis comprising:
    a femoral component having a pair of spaced apart condylar portions, each of the condylar portions having an inferior articulation surface and a superior surface, the femoral component further including
    a boss structure disposed between and connecting the condylar portions of the femoral component, the boss structure having a superior surface that is generally horizontally oriented in a transverse plane, and an opposed inferior surface,
    an aperture of a selected configuration extending between the inferior and superior surfaces of the boss structure, and
    first positioning means formed on at least one surface of the boss structure, adjacent the aperture, defining a plurality of transverse plane mounting positions for a femoral stem member;
    a washer element having a main body and an aperture extending therethrough, said washer element being mountable upon the inferior surface of the boss structure and having second positioning means for cooperating with the first positioning means to secure the washer element in one of the plurality of transverse plane mounting positions;
    a bolt having a head portion, and a neck region integrally formed with the head portion and extending outwardly therefrom, the neck region having dimensions such that it is able to fit within the aperture of the washer; and
    an elongate stem member for mounting within the medullary canal of a distal portion of a femur, the stem member having a proximal end and an open distal end for mounting to the boss structure.

12. The knee prosthesis of claim 11 further including a plurality of position indicia formed on the superior surface of the boss structure, the plurality of position indicia being arranged for visually indicating a position of the stem member at one of the plurality of transverse plane mounting positions.

13. The knee prosthesis of claim 11 wherein the first positioning means comprises one or more parallel grooves extending in a medial-lateral direction, and spaced apart from each other in an anterior-posterior direction, in the transverse plane, wherein each groove defines one of the plurality of transverse plane mounting positions.

14. The knee prosthesis of claim 13 wherein the second positioning means comprises a raised surface feature.

15. The knee prosthesis of claim 11 further comprising a collar having a distal region for mounting to the distal end of the femoral stem member and a proximal region for mounting on the superior surface of the boss structure.

16. The knee prosthesis of claim 15 wherein the collar has a main body and a central aperture disposed therethrough, the aperture seating at least a portion of the neck region of the bolt when disposed therein.

17. The knee prosthesis of claim 16 further including, a plurality of position indicia located relative to the first positioning means and arranged for visually indicating a position of the stem member at one of the plurality of traverse plane mounting positions.

18. The knee prosthesis of claim 17 wherein the plurality of position indicia includes first position markings on the superior surface of the boss structure, second position markings on the collar main body, said first and second markings cooperating to visually indicate the position of the stem member.

19. The knee prosthesis of claim 15 wherein the femoral stem member has an elongate main body that is generally curved along at least a portion of the main body.

20. The knee prosthesis of claim 19 further comprising first orientation indicia formed on the collar and second orientation indicia formed on the distal end of the stem member, said first and second orientation indicia cooperating to position said curved stem member in one of a plurality of positions in a sagittal plane.

21. The knee prosthesis of claim 11 wherein the aperture formed in the boss structure of the femoral component is elongated in the transverse plane, in an anterior-posterior direction.

22. The knee prosthesis of claim 11 further comprising orientation indicia for visually indicating an orientation of the stem member in a sagittal plane.

23. A modular knee prosthesis comprising:

a femoral component having a pair of spaced apart condylar portions, each of the condylar portions having an inferior articulation surface and a superior surface, a generally horizontally oriented boss structure having an inferior surface and an opposed superior surface, and a boss aperture extending between the inferior surface and superior surface;

a femoral stem component for mounting within the medullary canal of a distal portion of a patient's femur, the femoral stem component having a proximal end, and a distal end that is mountable to the boss structure; and means for securing the femoral stem component in one or more of a plurality of desired transverse plane mounting positions, the means for securing comprising one or more surface features associated with the boss structure and a mating element in the form of a washer element having a central aperture disposed therein, the mating element being directly or indirectly mountable upon the inferior surface of the boss structure and being interlockable with at least one of the surface features associated with the boss structure, an elongate bolt having a head portion and a neck portion, the neck portion being adapted to mount within the boss aperture and to extend into a distal portion of the femoral stem component.

24. The knee prosthesis of claim 23 wherein the one or more surface features on the mating element comprise a detent structure formed on a surface of the washer element that contacts the inferior surface of the boss structure.

* * * * *